US00PP25610P3

(12) United States Plant Patent
Lin

(10) Patent No.: US PP25,610 P3
(45) Date of Patent: Jun. 2, 2015

(54) ***PHALAENOPSIS* PLANT NAMED 'YOUNGHOME VENUS'**

(50) Latin Name: *Phalaenopsis*
Varietal Denomination: Younghome Venus

(71) Applicant: Young Home Orchid Co., Ltd., Pingtung (TW)

(72) Inventor: Chun-Teng Lin, Pingtung (TW)

(73) Assignee: Young Home Orchid Co., Ltd, Pingtung (TW)

( * ) Notice: Subject to any disclaimer, the term of this patent is extended or adjusted under 35 U.S.C. 154(b) by 0 days.

(21) Appl. No.: 13/986,264

(22) Filed: Apr. 17, 2013

(65) Prior Publication Data

US 2014/0317803 P1 Oct. 23, 2014

(51) Int. Cl.
*A01H 5/00* (2006.01)

(52) U.S. Cl.
USPC ..... Plt./311

(58) Field of Classification Search
USPC ..... Plt./311
CPC ..... A01H 5/00; A01H 5/02
See application file for complete search history.

*Primary Examiner* — June Hwu
*Assistant Examiner* — Keith Robinson
(74) *Attorney, Agent, or Firm* — Muncy, Geissler, Olds & Lowe, P.C.

(57) ABSTRACT

A new and distinct cultivar named 'Younghome Venus' is disclosed, characterized by white flowers with red purple shaded around the column, a freely flowering habit, an upright, freely branching and sturdy flowering stem, strong growth ability and disease resistance.

2 Drawing Sheets

FIELD OF THE INVENTION

Botanical classification: *Phalaenopsis.*

Variety denomination: 'Younghome Venus'.

The present invention relates to botanical classification/cultivar designation: *Phalaenopsis* Orchid cultivar Younghome Venus.

BACKGROUND OF THE INVENTION

The present invention comprises a new and distinct cultivar of *Phalaenopsis* Orchid, and hereinafter referred to by the cultivar name, 'Younghome Venus'.

The new cultivar is a product of a planned breeding program conducted by the Inventor in Pingtung, Taiwan. The objective of the breeding program is to create new uniform pot-type *Phalaenopsis* Orchid cultivars having attractive flower coloration.

Asexual propagation by tissue culture in a laboratory in Pingtung, Taiwan has been used to increase the number of plants for evaluation and has demonstrated that the unique combination of characteristics as herein disclosed for the new *Phalaenopsis* Orchid are firmly fixed and are retained through successive generations of asexual reproduction.

SUMMARY OF THE INVENTION

The following traits have been repeatedly observed and are determined to be basic characteristics of new cultivar which in combination distinguish this *Phalaenopsis* Orchid as a new and distinct cultivar:

1. White flower with red purple color shaded around the column.
2. Freely flowering habit.
3. Upright, freely branching and sturdy flowering stem.
4. Strong growth ability and disease resistance.

Plants of the new cultivar differ primarily from plants of the parent cultivars, which are 'Hsinying Mount' (not patented) and 'Maki Watanabe' (not patented), in flower color.

Plants of 'Younghome Venus' can be compared to the 'Sogo Yukidian' (not patented) in the following characteristics:

1. Plants of the new *Phalaenopsis* orchid are smaller than plants of the cultivar 'Sogo Yukidian'.
2. Plants of the new *Phalaenopsis* orchid have shorter spikes than plants of the cultivar 'Sogo Yukidian'.
3. Plants of the new *Phalaenopsis* orchid have smaller flower size than plants of the cultivar 'Sogo Yukidian'.
4. The petals for plants of the new *Phalaenopsis* orchid are white and red purple around the column, while plants of the cultivar 'Sogo Yukidian' is white.
5. The new *Phalaenopsis* orchid has orange labellum and plants of the cultivar 'Sogo Yukidian' are yellow.

BRIEF DESCRIPTION OF THE DRAWINGS

Colors in the photographs may appear different from the color values that appear in the detailed botanical description which more accurately describe the new cultivar.

DETAILED DESCRIPTION OF THE PREFERRED EMBODIMENTS

Figure 1:
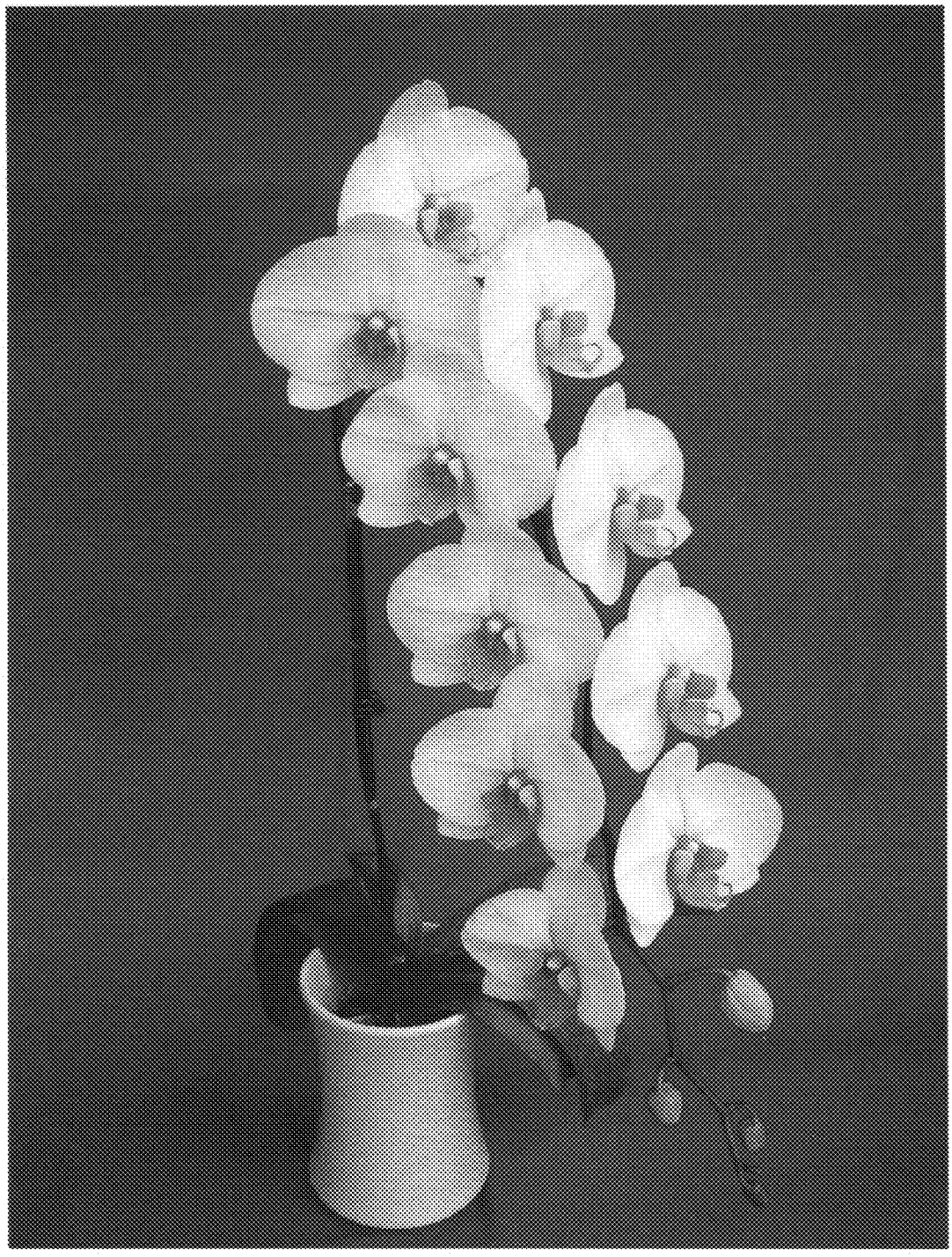
FIG. 1 is a side view of a plant of 'Younghome Venus' flowering in the pot of 12 cm.
Figure 2:
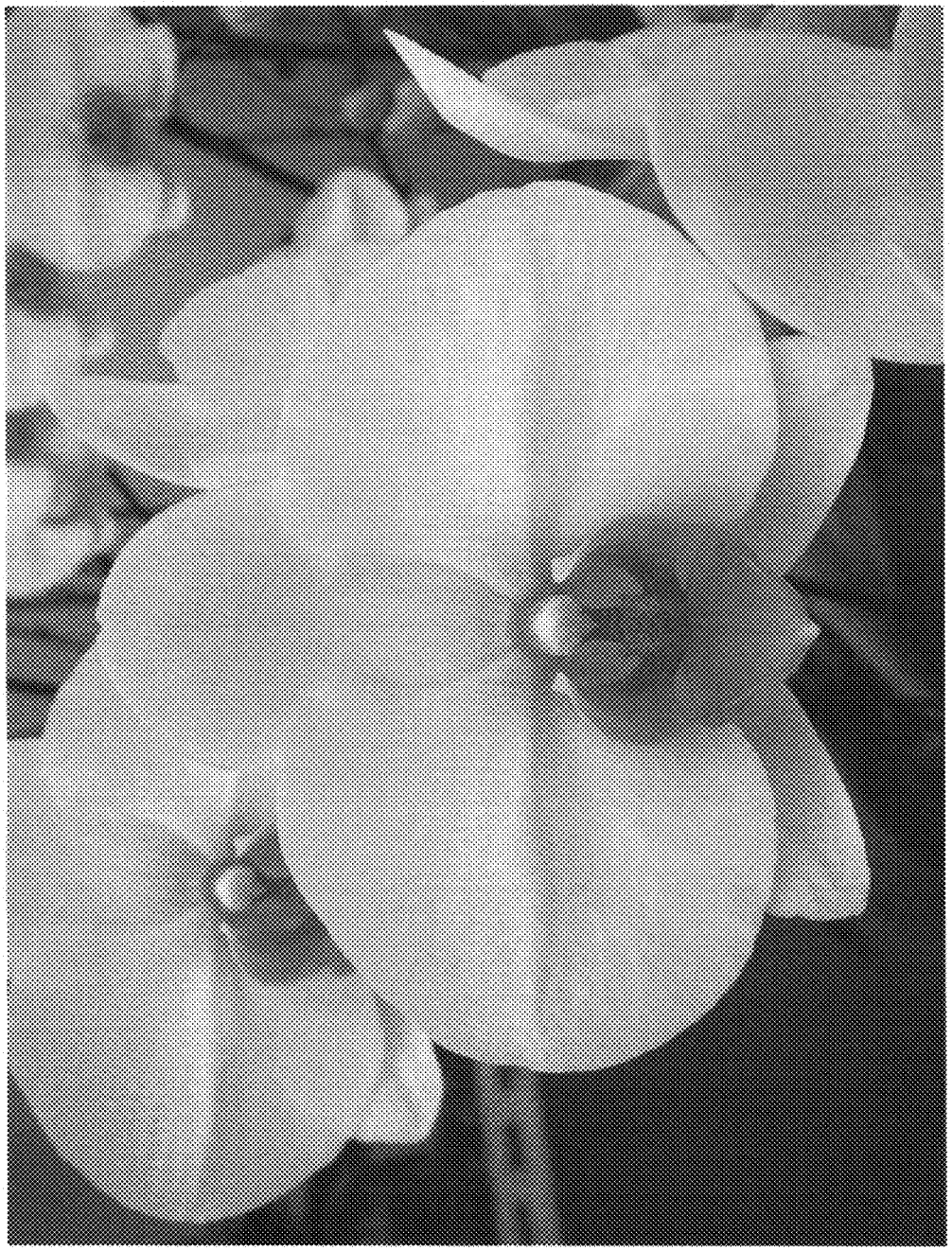
FIG. 2 is a close-up view showing the characteristics of the flower.

'Younghome Venus' has not been observed under all possible environmental conditions. The phenotype may vary significantly with variations in environment such as temperature and light intensity, without however, any change in genotype. In the following description, color reference are made to The Royal Horticultural Society (R.H.S.) Colour Chart, 2007, fifth edition, except where terms of ordinary dictionary significance are used.

'Younghome Venus' used for aforementioned photographs and following detailed botanical description were 11 months old and grown in 12 cm containers in Pingtung, Taiwan, in a controlled green house with day temperature about 26~29° C., night temperature about 18~20° C., and light level about 15,000~20,000 lux. The photographs and detailed botanical description were taken during the winter.

Parentage:

*Seed*.—'Hsinying Mount'.

*Pollen*.—'Maki Watanabe'.

Compared with parent cultivars: Plants of 'Younghome Venus' can be compared to 'Hsinying Mount' (not patented) in the following characteristics:

1. The petal main color of 'Younghome Venus' is white (RHS NN155D) while the petal main color of 'Hsinying Mount' is white (RHS 155C).
2. The leaf color of 'Younghome Venus' is green (RHS N137C) with purple (RHS N79B) discoloration but the leaf color of 'Hsinying Mount' is green (RHS N134A).
3. The petal pattern color around the column of 'Younghome Venus' is red purple (RHS N74B) but the petal pattern color around the column of 'Hsinying Mount' is red purple (RHS N80B).
4. The color of the base of labellum of 'Younghome Venus' is light orange (RHS 24B) while the color of the base of labellum of 'Hsinying Mount' is red purple (RHS 71A).
5. The color of the tip of labellum of 'Younghome Venus' is orange (RHS 24A) but the color of the base of labellum of 'Hsinying Mount' is red purple (RHS 72A).
6. When planted in a 3.5 inch flowerpot, the double spike rate of 'Younghome Venus' is about 90% but that of 'Hsinying Mount' is about 40 to 60%.

Plants of 'Younghome Venus' can be compared to 'Maki Watanabe' (not patented) in the following characteristics:

1. The petal main color of 'Younghome Venus' is white (RHS NN155D) but the petal main color of 'Maki Watanabe' is light purple (RHS 75D).
2. The leaf color of 'Younghome Venus' is green (RHS N137C) with purple (RHS N79B) discoloration, but the leaf color of 'Maki Watanabe' is green (RHS N141B).
3. The petal pattern color around the column of 'Younghome Venus' is red purple (RHS N74B) but the petal pattern color around the column of 'Maki Watanabe' is red purple (RHS 77B).
4. The color of the base of labellum of 'Younghome Venus' is light orange (RHS 24B) but the color of the base of labellum of 'Maki Watanabe' is white (RHS NN155B) with yellow orange (RHS 17A).
5. The color of the tip of labellum of 'Younghome Venus' is orange (RHS 24A) but the color of the base of labellum of 'Maki Watanabe' is white (RHS NN155B).
6. When planted in a 3.5 inch flowerpot, the double terrier rate of 'Younghome Venus' is about 90% but that of 'Maki Watanabe' is about 60%.

Propagation: Asexual propagation by tissue culture.

Plant description:

*Plant shape*.—Two-ranked leaves affixed to a short central stem (monopodial growth). Single flowers arranged on upright and sturdy flowering rancemes.

*Plant height, soil level to top of foliar plane*.—About 13 to 15 cm.

*Plant height, soil level to top of inflorescences*.—About 62 to 67 cm.

*Plant diameter*.—About 35 to 45 cm.

Flowers per stem: Approximately 8 to 11.

Foliage description:

*Leaf arrangement*.—Alternate.

*Quantity per plant*.—About 6 to 8.

*Length*.—About 25 to 35 cm.

*Width*.—About 6 to 8 cm.

*Leaf thickness*.—About 0.02 to 0.04 cm.

*Shape*.—Elliptic, elongated.

*Apex*.—Oblong, obtuse.

*Base*.—Cuneate.

*Margin*.—Entire.

*Aspect*.—Mostly flat and folded upward from the midrib.

*Texture, upper and lower surfaces*.—Leathery, thick.

*Venation*.—Parallel, veins are sunken within the lamina.

*Color (upper surface)*.—Green (RHS N137C) with purple (RHS N79B) discoloration.

*Color (lower surface)*.—Green (RHS N137C) with purple (RHS N79B) discoloration.

Flower description:

*Inflorescence type*.—Compound raceme.

*Flower type*.—Single zygomorphic flowers arranged in racemes. Flowers roughly pentagonal in shape.

*Flower arrangement*.—Compound alternate

*Flowering stems*.—Upright, freely branching and sturdy.

*Flowering habit*.—Plants freely flowering; plants typically produce 1 to 2 branched flowering stems with at least 8 to 11 flowers each.

*Fragrance*.—Negative.

*Natural flowering season*.—From January to April in Taiwan.

*Post-production longevity*.—Plants of 'Younghome Venus' maintain good leaf and flower substance for about 1.5 to 2 months on the plant under interior environmental conditions.

*Inflorescence length*.—About 12 to 34 cm.

*Inflorescence diameter*.—About 16 to 20 cm.

*Flower diameter*.—About 10 to 11 cm.

*Flower depth*.—About 3 cm.

*Flower bud shape*.—Orbicular.

*Flower bud height*.—About 2 cm.

*Flower bud diameter*.—About 1 cm.

*Flower bud color*.—Yellow-green (RHS146B).

Petals:

*Number of petals*.—2 per flower.

*Length*.—About 6.5 cm.

*Width*.—About 5 cm.

*Shape*.—Obovate.

*Apex*.—Rounded.

*Base*.—Attenuate and fused with the column.

*Margin*.—Attenuate and fused with the column.

*Texture, upper and lower surfaces*.—Smooth.

*Petal arrangement*.—Two bilateral symmetry petals, an upper petal located between the two bilateral symmetry petals, and two petals each arranged at 45 degrees and located under the two bilateral symmetry petals respectively.

*Petal main color*.—White (RHS NN155D).

*Petal pattern color*.—Red purple (RHS N74B) around the column.

Labellum:

*Length*.—About 2.3 cm.

*Diameter*.—About 2 cm.

*Shape*.—Deeply three-lobed with two prominent callosities on the upper surface at the central junction of the lateral lobe and the base of the middle lobe. The shape of the middle lobe is rhombic with upend hook shape and whiskers at the apex.

*Base color of the apical lobe*.—Light orange (RHS 24B).

*Tip color of the apical lobe*.—Orange (RHS 24A).

*Color of lateral lobe*.—Orange (RHS 23C) with red-purple (RHS 59B) stripe.

*Color of callus of prominent structure on lip*.—Light orange (RHS 24B) with red-purple (RHS 59B) spots.

Sepals:

*Quantity*.—3 per flower.

*Dorsal sepal length*.—About 5.5 cm.

*Lateral sepal length*.—About 5 cm.

*Dorsal sepal diameter*.—About 4 cm.

*Lateral sepal diameter*.—About 3 cm.

*Shape*.—Ovate.

*Apex*.—Round.

*Base*.—Attenuate and fused with the column.

*Margin*.—Entire.

*Texture, upper and lower surfaces*.—Velvety and smooth.

*Dorsal sepal main color*.—White (RHS NN155D).

*Dorsal sepal pattern color*.—Red purple (RHS N74B) around the column.

*Lateral sepal main color*.—White (RHS NN155D).

*Lateral sepal pattern color*.—Green-yellow (RHS 1D).

Peduncles:

*Length*.—About 30 to 36 cm.

*Diameter*.—About 0.6 cm.

*Aspect*.—Upright.

*Strength*.—Strong.

*Texture*.—Smooth, glabrous.

*Color*.—Green (RHS N137A).

Pedicels:

*Length*.—About 3 cm.

*Diameter*.—About 3 mm.

*Aspect*.—About 75° from vertical, two spikes about 55° from vertical.

*Strength*.—Strong, sturdy.

*Texture*.—Smooth, glabrous.

*Color*.—Green (RHS N137A).

*Color towards the base*.—Green (RHS N137A).

Reproductive organs:

*Column*.—

*Length*.—About 0.7 cm.

*Diameter*.—About 6 mm.

*Color*.—The lip is orange (RHS 23C) with red-purple (RHS 59B) stripe, lower part is white (RHS 155D).

*Pollinia*.—Quantity of pollen masses — 2.

*Diameter*.—About 2 mm.

*Color*.—White (RHS NN155D).

*Ovary*.—

*Length*.—About 5 mm.

*Diameter*.—About 3.5 mm.

*Color*.—Grayed-red (RHS 182C).

*Root*.—It takes 14 days for plants growing in tissue culture to initiate roots.

*Diameter*.—About 6 mm.

*Color*.—RHS 138A.

Disease/pest resistance: Strong disease resistance for diseases such as anthracnose and bacterial brown spot, but no specific resistance or susceptibility to pests has been observed.

Temperature tolerance: Plants of the new *Phalaenopsis* Orchid have been observed to be tolerant to temperatures from 16~35° C. The flower has been observed to be tolerant from 20~28° C.

What is claimed is:

1. A new and distinct cultivar of *Phalaenopsis* orchid plant named 'Younghome Venus' as illustrated and described.

* * * * *